United States Patent [19]

Shoher et al.

[11] Patent Number: 5,730,600
[45] Date of Patent: Mar. 24, 1998

[54] METHOD FOR FORMING A DENTAL RESTORATION

[76] Inventors: Itzhak Shoher; Aharon E. Whiteman, both of P.O. Box 58069, Tel Aviv 61580, Israel

[21] Appl. No.: 570,403

[22] Filed: Dec. 11, 1995

Related U.S. Application Data

[63] Continuation-in-part of Ser. No. 229,358, Jul. 25, 1994, Pat. No. 5,593,305, which is a continuation-in-part of Ser. No. 5,595, Jan. 19, 1993, Pat. No. 5,332,622.

[51] Int. Cl.$^6$ .................................................. A61C 5/10
[52] U.S. Cl. .................................. 433/223; 433/215
[58] Field of Search .............................. 433/215, 218, 433/223, 228.1; 75/228; 29/160.6; 428/212

[56] References Cited

U.S. PATENT DOCUMENTS

| | | | |
|---|---|---|---|
| 2,839,379 | 6/1958 | Erasmus | 428/613 |
| 3,502,466 | 3/1970 | Vickery | 419/27 |
| 3,623,541 | 11/1971 | Schmitz | 164/337 |
| 3,845,807 | 11/1974 | Koon | 164/255 |
| 4,355,980 | 10/1982 | Dwight | 433/228.1 |
| 4,468,251 | 8/1984 | Hausselt et al. | 433/218 |
| 4,554,218 | 11/1985 | Gardner et al. | 428/567 |
| 4,676,751 | 6/1987 | Shoher et al. | 433/218 |
| 4,698,021 | 10/1987 | Shoher et al. | 433/218 |
| 4,742,861 | 5/1988 | Shoher et al. | 164/80 |
| 4,814,008 | 3/1989 | Shoher et al. | 433/207 |
| 4,846,718 | 7/1989 | Rieger | 433/218 |
| 4,940,637 | 7/1990 | Shoher et al. | 433/218 |
| 5,094,689 | 3/1992 | Shuemke et al. | 106/35 |

Primary Examiner—John J. Wilson

[57] ABSTRACT

The present invention is a method for forming, repairing or restoring a dental restoration which includes the steps of forming a base material of high-fusing temperature metal particles, low fusing temperature metal particles and a volatile binder substantially or entirely of wax; applying the base material to a die; shaping the base material upon said die into the desired configuration of the dental restoration; removing the configured base material from the die; combining particles of activated carbon with investment material to form a combined dental investment material having activated carbon in a concentration above at least 0.005 wt. % of the combined dental investment material; filling the configured base material with the combined dental investment material; heat treating the shaped base material in the investment at temperatures up to 1200° C. to vaporize the volatile binder from the base material for forming a porous structure with a void volume of at least 20%; and filling the porous structure with a filler material to form a finished dental coping.

11 Claims, 5 Drawing Sheets

METHOD FOR FORMING A DENTAL RESTORATION

FIELD OF THE INVENTION

This invention is a continuation-in-part of U.S. patent application Ser. No. 08/229,358 filed Jul. 25, 1994, now U.S. Pat. No. 5,593,305 which is, in turn, a continuation-in-part of U.S. patent application Ser. No. 005,595 filed Jan. 19, 1993 now U.S. Pat. No. 5,332,622 and relates to a method for forming and/or repairing dental restorations.

BACKGROUND OF THE INVENTION

In crown and bridge prosthodontics, metal copings are conventionally used to provide the essential structural strength and rigidity necessary for a dental restoration to resist the forces of mastication. In crowns, inlays, onlays and fixed partial prosthesis dental restorations, the metal coping forms the understructure, over which a conventional tooth coloring material of porcelain or acrylic is applied and heat treated to form a fired-on coating. The coating of porcelain or acrylic is formed over the coping solely for aesthetics to simulate the look of natural teeth. To the dental patient, color and the overall appearance of the dental restoration are critical factors in the satisfaction of the restoration. Accordingly, the color of the metal coping is important and should enhance the aesthetics of the restoration. For a ceramic-to-metal dental restoration, the metal coping should enhance the porcelain by providing a background color contrast.

In Applicant's U.S. Pat. No. 5,234,343 entitled Moldable Dental Material and Method, Ser. No. 07/887,245, filed May 19, 1992, the disclosure of which is herein incorporated by reference, a dental material composition is taught which can be readily shaped or molded into any desired shape for repairing and/or forming a dental restoration. The composition of the material and method of application is taught in Applicant's earlier U.S. Pat. Nos. 4,742,861 and 4,990,394. In general, the dental material is preferably composed of both high fusing temperature metal particles and low fusing temperature metal particles combined in a matrix with a volatile binder for forming a dental restoration directly on a die or model of the tooth or teeth to be restored. The material is shaped on the die into a desired configuration and heat-treated at a temperature to vaporize the binder and to melt, or substantially melt, the low-fusing temperature metal particles resulting in a porous, sponge-like structure having the shape it was given prior to heat treatment. A low-melting temperature filler material, preferably of gold, is then melted into the sponge-like structure to form a solid metal coping, with a configuration identical to the configuration of the shaped material on the die before heat treatment and without experiencing distortion and/or shrinkage.

The solidified metal should possess a desirable color, which is reproducible with high accuracy, for use in forming a dental restoration. Heretofore, the process was sensitive to temperature variations in the furnace during heat treatment and even minor variations in temperature during the heat-treatment procedure would permit some oxidation of the metals to occur, which could deleteriously affect its color, and even more seriously, could inhibit the flow of filler material into the porous sponge, which would affect the size of the solidified sponge. In fact, even the type of furnace used or its condition was able to affect the ability to accurately control the temperature during the heat-treatment procedures. Although sophisticated furnace temperature control equipment is commercially available, the implementation of such equipment is costly and would be unacceptable to the dental practitioner. The sensitivity to temperature variation also limited the process to the fabrication within the furnace of one restoration at a time which made the process very costly.

In U.S. Pat. No. 5,332,622 the above identified temperature sensitivity problem was solved by the addition of activated carbon to the dental material composition. However the process was limited in a practical sense to the use of a refractory die. Although dental laboratories conventionally use refractory dies this is not cost effective or practical in the fabrication of only a limited number of restorations or custom restorations, of for example 1–3, at one time. In this situation it is preferred for the dental laboratory to use a conventional stone working die or any other type of conventional non-refractory working die which is not to be heat treated. A method has been discovered in accordance with the present invention for forming and/or repairing dental restorations utilizing the principles and methodology taught in Applicant's earlier U.S. Pat. Nos. 5,234,343, 4,742,861 and 4,990,394 which overcomes the above identified temperature sensitivity problems during heat treatment for use with a non-refractory working die. This method is particularly suited to the fabrication of a limited number of restorations at one time where a non-refractory stone, metal or polymer die is preferred by the laboratory technician or dentist.

SUMMARY OF THE INVENTION

The method of the present invention for forming, repairing or restoring a dental restoration can be readily practiced either at the dental laboratory or by the dentist in the dental office assuming a dental furnace is available.

The method of the present invention comprises the steps of:

forming a base material comprising high-fusing temperature metal particles and a volatile binder substantially or entirely of wax;

applying the base material to a die;

shaping the base material upon said die into a desired configuration;

removing the shaped base material from the die;

combining particles of activated carbon with an investment material to form a dental investment material having activated carbon in a concentration above at least 0.005 wt. %;

filling the dental investment material into the shaped base material;

heat treating the shaped base material containing the dental investment material at temperatures up to 1200° C. to vaporize the volatile binder from the base material for forming a porous structure with a void volume of at least 20%; and filling the porous structure with a filler material to form a finished dental coping.

BRIEF DESCRIPTION OF THE DRAWINGS

Additional advantages of the present invention will become apparent from the following detailed description of the invention when read in conjunction with the accompanying drawings of which.

DETAILED DESCRIPTION OF THE INVENTION

Figure 1:
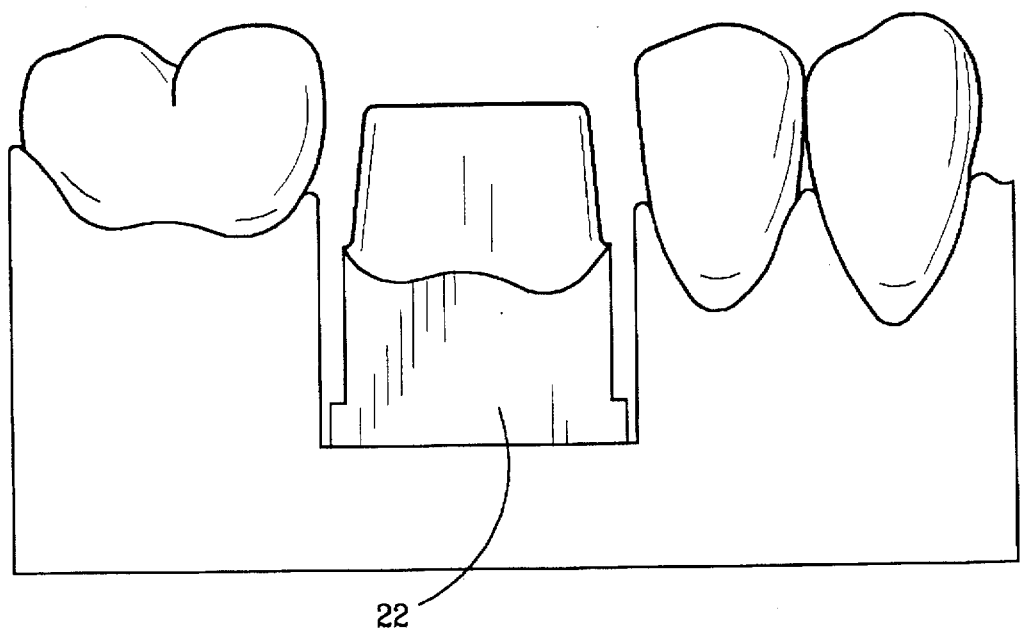
FIG. 1 is a perspective view of a non-refractory working die shown in a conventional stone working model for practicing the present invention.
Figure 2:
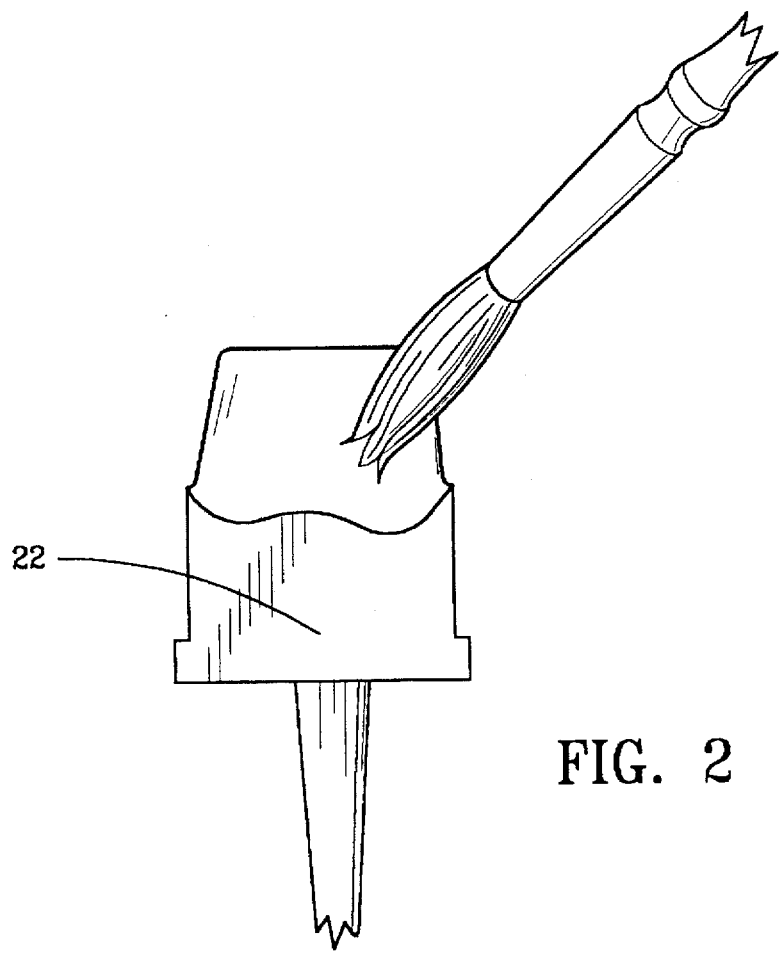
FIG. 2 is a perspective of the working die of FIG. 1 and being removed from the model for illustrating the preferred preparatory step of painting a separating layer over the die.
Figure 3:
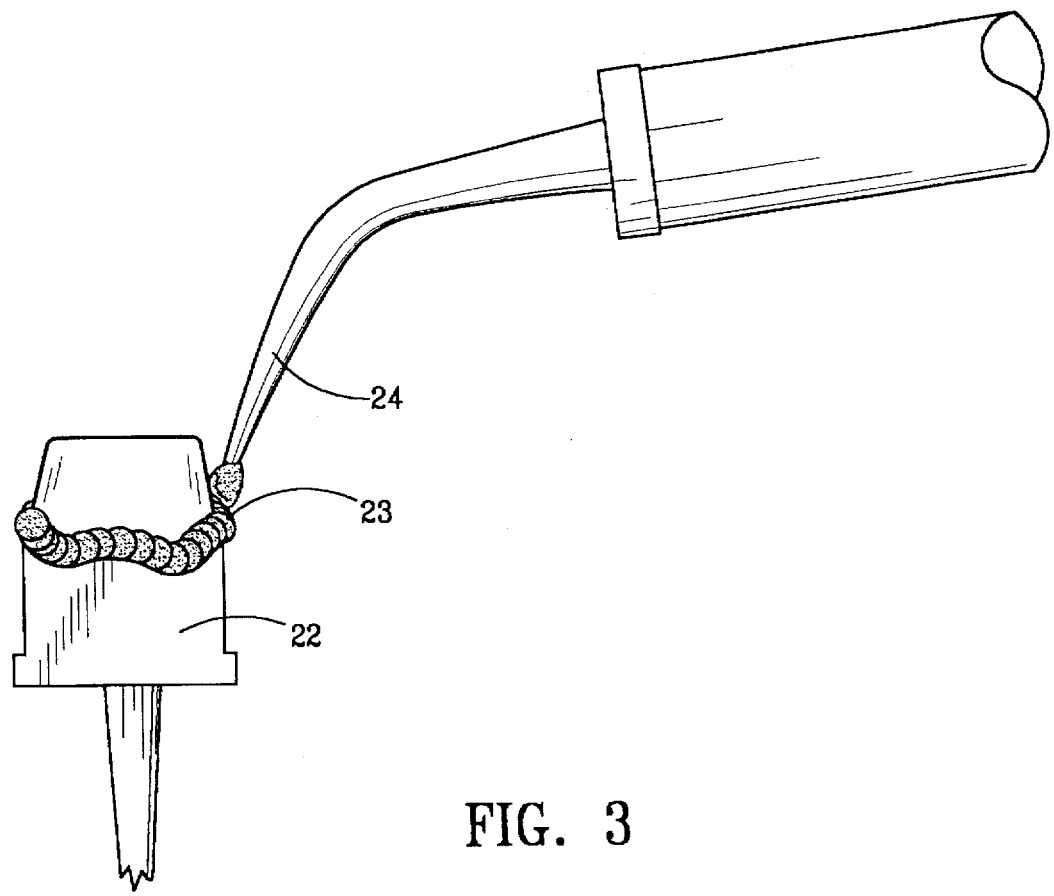
FIG. 3 is an illustration in perspective of the preferred method of applying base material to the non-refractory working die of FIG. 2.

The method of the present invention is an improvement of U.S. patent application Ser. No. 08/229,358 filed Jul. 25, 1994, now U.S. Pat. No. 5,593,305 which permits the use of a moldable dental material as generally taught in U.S. Pat. Nos. 5,234,343, 4,742,861 and 4,990,394 for forming, repairing or restoring dental restorations using any conventional stone, metal or polymer die.

In U.S. patent application Ser. No. 08/229,358 filed Jul. 25, 1994 particles of activated carbon are preferably added to the base material of the dental composition prior to application of the base material to the working die. In the teaching of this patent the working die is a refractory die. In accordance with the present invention the particles of activated carbon are preferably added to a conventional investment material and the working die may be any conventional stone, metal or polymer die. The applied base material, after it is shaped, is invested with investment material and heat treatment as will hereafter be explained in greater detail.

The method of the present invention is practiced by first forming a base material of a high-fusing temperature metal component, a low fusing dental metal component and a volatile binder substantially or entirely of wax. The high-fusing temperature metal component is critical to the composition of the base material and may be a single metal or metal alloy, preferably of precious metals such as platinum and palladium in any desired proportion to one another from zero to one hundred percent and may include gold in any desired concentration. Additional constituents may be added such as Ag, Cu, Mg, Al, Zn, and other metals of the platinum group of elements of the third and fourth group of elements. The total weight percent of the elements other than gold, silver, and the platinum group metals should not exceed ten percent. Gold may be added in any proportion to the high-fusing temperature metal component to increase the affinity of the high-fusing temperature metal component to the low-fusing temperature metal component or to itself in the absence of the low fusing component. In the latter instance gold may represent the major constituent of the high fusing metal composition and depending upon its concentration will lower the melting temperature of the high fusing component to as low as 900°–950° C.

The high fusing particles should also be of an irregular shape preferably in the form of flakes, that is, platelets and should be very thin. The size and dimensions of the irregular, flake-like particles play an important function. The very thin platelets of high-fusing particles interleave one another to provide sufficient mechanical integrity to form a porous structure during heat treatment and even without the presence of low-fusing particles will surprisingly retain its structure after heat treatment with minimal shrinkage. It is postulated that even without low-fusing particles, the heat-treatment operation forms localized, autogenous joints which maintain the structural integrity of the porous structure after heat treatment. However, the porous structure formed with the use of low-fusing particles as part of the composition is still preferred. Moreover it is preferred but not critical to the invention that at least fifty percent (50%) of the high-fusing metal particles have a thin, cross-sectional, average thickness of less than about 1.5 microns. The following test, in combination with the examples given below, should be employed to determine if fifty percent (50%) of the high-fusing particles meet this 1.5 micron thickness limitation: (a) the surface area of the largest two-dimensional surface (or its "projected image") for each of the high-fusing particles should be measured, (b) the total surface area of all of the high-fusing particles should be calculated, and (c) the cumulative surface area of the high-fusing particles below 1.5 microns in average thickness should then be divided by the computed total surface area. The surface area calculation is a simple two-dimensional measurement of the area circumscribing the flat, planar surface containing the largest two-dimensional image of each particle. If the planar geometry of the particle were rectangular, the surface area would simply be the length times the width. As an illustration, assume a high-fusing particle flake geometry of 5 $\mu$(long)×1 $\mu$(wide)×3 microns thick. The largest two-dimensional surface area is 5 $\mu$×10 $\mu$. For a second illustration, assume a geometry of 20 $\mu$(long)×5 $\mu$(wide)×1 $\mu$(thick). Again, the largest two-dimensional surface area is 20 $\mu$×5 $\mu$. As a third example, assume a flake geometry of a ball having a diameter of 20 microns. A two-dimensional projected image would be a circle having a surface area of $\pi r^2$ or $\pi 100$. The taking of a "projected image" of the largest two-dimensional surface maybe necessary based on undulations and irregularities in the flake surfaces which would otherwise complicate the surface area calculation. The cumulative total of the surface area for all of the particles is preferably determined by statistical analysis. There are commercial analytical instruments and techniques available which may be used for computing the surface area of the particles. Preferably, most of the particles will have a very thin cross-sectional thickness of less than about 1.5 microns. However, since it is possible to break larger particles into many smaller particles, it is necessary to make a surface area measurement to determine if at least fifty percent (50%) of the total population of the high-fusing particles in the composition are of proper thickness.

As stated above although the base material may be limited to only high-fusing metal particles it is preferred to include low-fusing metal particles to enhance the wetting of the high-fusing particles during heat treatment. The particles of low-fusing temperature metal are composed preferably of gold or a gold alloy, with gold as the major constituent. The preference for gold as the major constituent of the low-fusing component is based on its known characteristics of workability, biocompatibility, nonoxidizing properties, and color. The low-fusing metal particles must, of course, have a melting temperature below that of the high-fusing metal particles. The preference for gold as the major constituent of the low-fusing component is based on its known characteristics of workability, biocompatibility, non-oxidizing properties and color. The low fusing metal particles must, of course, have a melting temperature below that of the high fusing metal particles. When the high-fusing metal particles possess a flake-like geometry and are very thin, they overlap to form a lattice network of particles. This assures adequate strength even when the composition is thinned down near the dental margin without flaking. The thin flakes also assure a compact, open-pore structure of uniform porosity, which also provides a greater reliability of dimensional control over the voids in the heat-treated structure.

Upon heat treatment of the base material, the binder should vaporize to leave a porous, sponge-like structure having a capillary network of multiple voids uniformly distributed throughout the structure, with a void volume preferably of at least twenty percent (20%), and up to eighty percent (80%).

Although the binder may be any suitable vehicle which will vaporize upon heat treatment to facilitate the formation of a porous structure dental wax is preferred. The binder may include organic or inorganic components to control the malleability of the dental material. The term "wax," for purposes of the present invention, means any natural wax, mineral wax, or organic wax, or combination thereof. The wax composition is not critical as long as it melts relatively cleanly without leaving a residue. The viscosity of the wax is also not critical although for purposes of the present invention a relatively viscose or "hard" wax should be used. The concentration of the wax binder is preferably high enough to assure a void volume of at least twenty percent (20%). When the concentration of binder is at least twenty percent (20%) by volume, the relationship between void volume and binder is substantially one-to-one.

Figure 4:
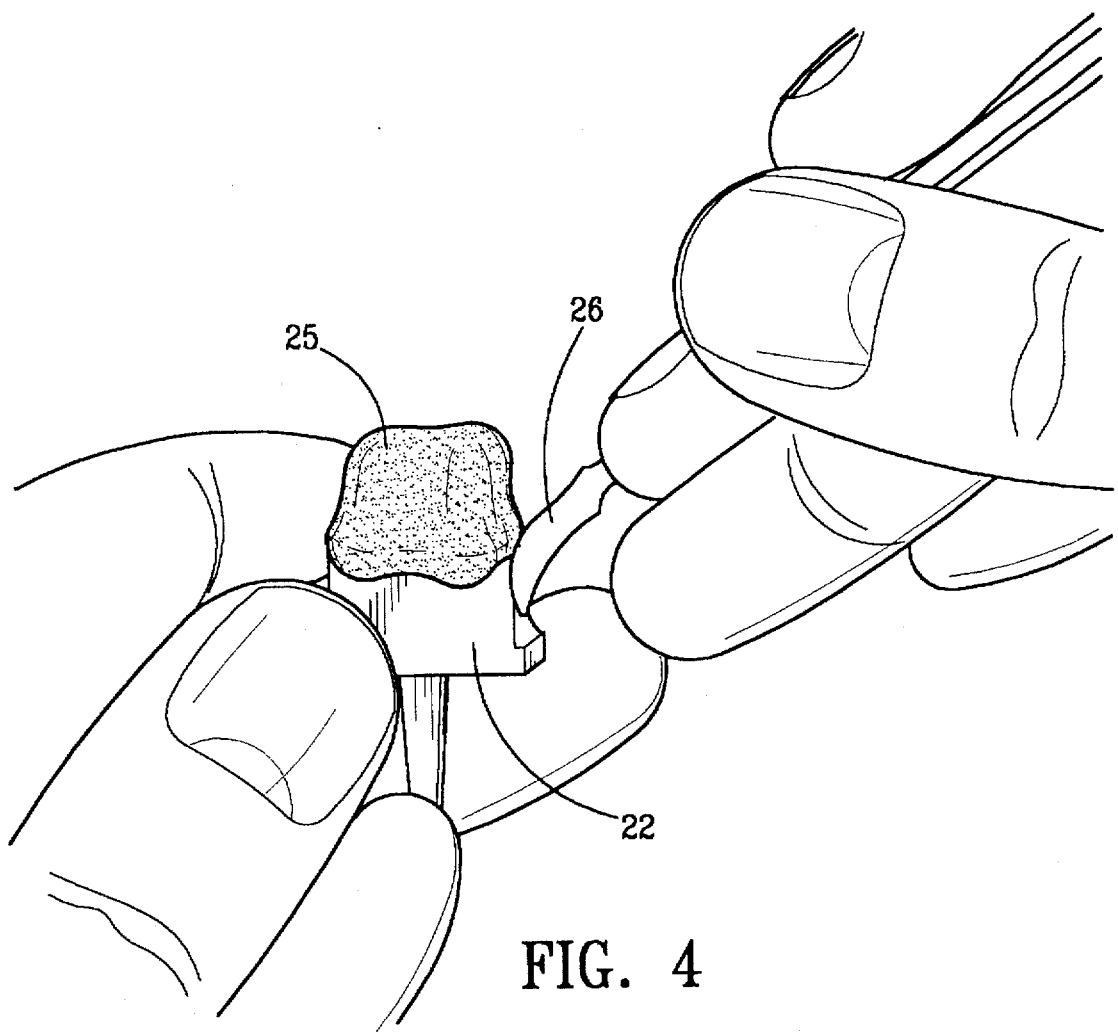
FIG. 4 is a further illustration in perspective of the procedure for shaping the base material after application upon the non-refractory working die of FIG. 3.
Figure 5:
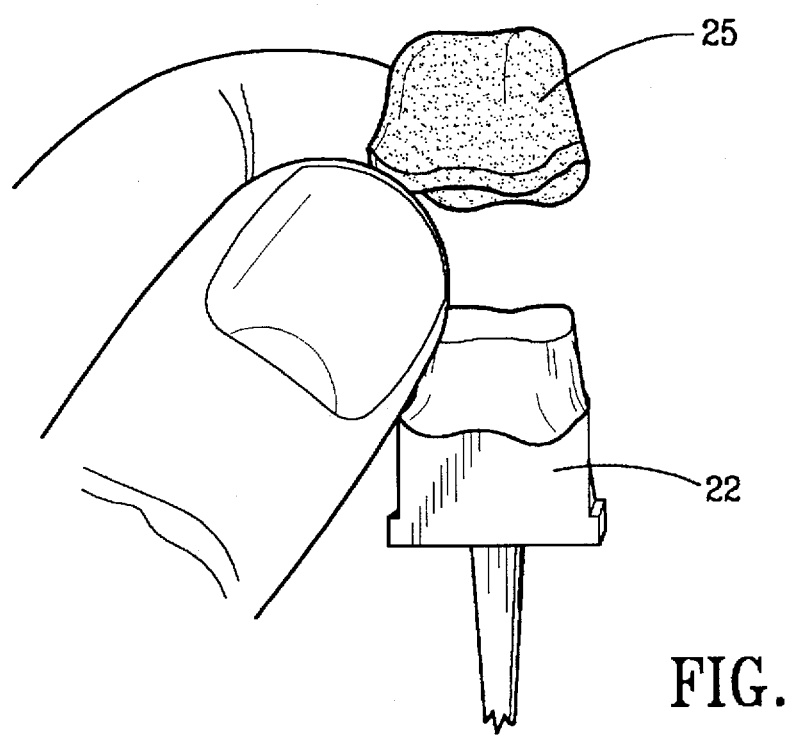
FIG. 5 is yet another illustration in perspective of the shaped base material having the form of a finished coping upon its removal from the working die of FIG. 4.

The base material of the present invention is shaped upon a working die which may be composed of stone, metal or polymer. A conventional stone working model of dental teeth is shown in FIG. 1 with a removable stone working die 22. The die 22 may be composed from a refractory or non-refractory composition. Initially it is preferred to apply a conventional isolation material 15 over the working die 22 using e.g. a brush 16 so as to facilitate the separation of the base material from the working die 22 after shaping as shown in step 5. The use of a liquid or semi-liquid isolation material is very conventional in dentistry and typically used with standard investing and casting procedures. The base material 23 is preferably applied to the working die 22 using an electrically heated wax spatula 20 so that the base material 24 may be fed or applied by the spatula 20 to the working die 22 at an elevated temperature above that of room temperature to control the ease of application. After applying the base material 23 to the working die 22 it is shaped to form a desired configuration 25, preferably in the form of a dental coping, as shown in FIG. 4 using a hand wax carver or other conventional implement. The shaped base material 25 is then removed from the working die 22 as shown in FIG. 5 in preparation for investing.

Activated carbon particles are then added to a conventional dental investment material or to any conventional industrial investment material preferably for high temperature application. Activated carbon is a well-known, porous, carbonaceous material formed by heat-treating carbon or subjecting it to reaction with gases, sometimes adding chemicals, for example, zinc chloride, during or after carbonization, in order to increase its porosity. Its high porosity results in a very high surface area of many orders of magnitude larger than its untreated surface area. Activated carbon has a large absorption capacity to different gases. The carbonaceous particles from which activated carbon is formed may be of any conventional carbon material, including carbon black, coke flour, calcined lamp black flour, and the like. Suitable amounts of the activated carbon particles to be added to the dental investment material may range from five-thousands of one percent (0.005%) of the weight of the investment material used in investing the shaped base material 25 to about five percent (5%) of the weight of the investment material. Finely divided particles of activated carbon is preferred in particle sizes of less than 250 microns average. The activated carbon particles functions both as a reducing agent to assist in thew formation of the "sponge" i.e. high void volume coping and to assist the filler in filling in the capillary network formed by the base material during the heat-treatment procedures. The activated carbon substantially burns during heat treatment leaving little or no residue. Carbonaceous materials other than activated carbon are not suitable for satisfying the above objectives in the present invention and therefore even if present are of no avail.

Figure 6:
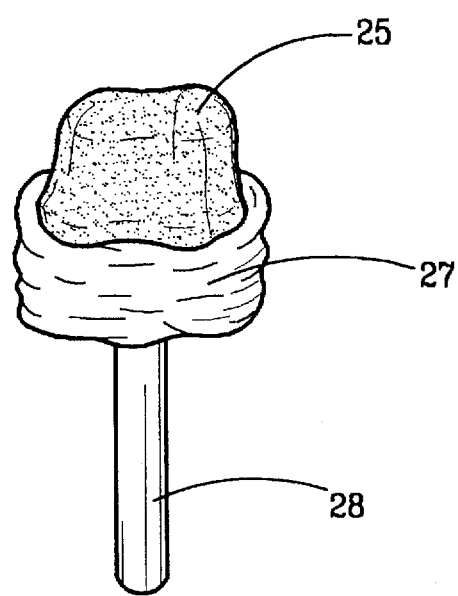
FIG. 6 is a perspective view of the shaped base material invested in the dental investment material prior to heat treatment.
Figure 7:
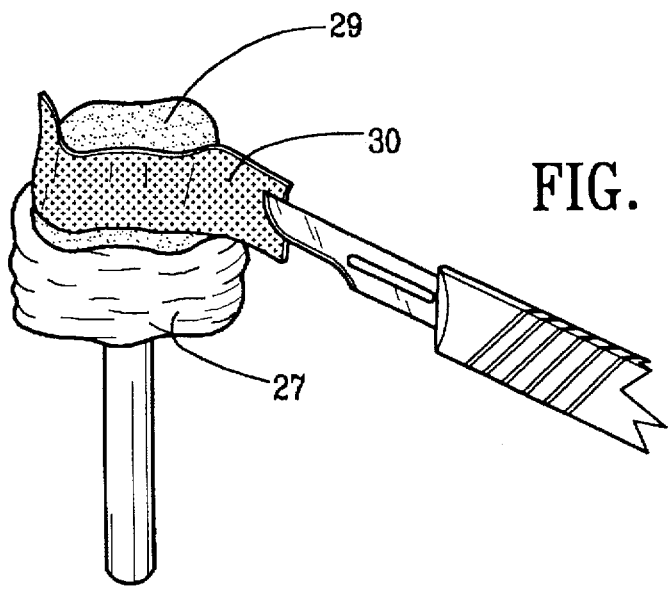
FIG. 7 is an illustration in perspective of the preferred method for adding filler material to the invested coping after heat treatment.

The shaped base material 25 is filled with investment material containing activated carbon 27 as shown in FIG. 6. A supporting pin 28 may be used to facilitate placement of the invested base material 25 on a firing tray (not shown) for insertion into a furnace (not shown). The invested base material 25 is then heat treated to convert the base material into a porous structure 29 of identical shape and without distortion. The porous structure 29 has a high void volume of above at least 20% and preferably over 30% void volume although the porosity may be as high as 80%. The heat-treatment for the base material may be done in stages generally between 500° C. and 1200° C. The total heat treatment for all the heat treatment stages of the base material totals generally less than 30 minutes and preferably less than 15 minutes.

A filler material is melted into the voids of the heat-treated porous structure 29 to solidify the structure for forming the final dental restoration. The filler material may be any suitable ceramic or metal composition, preferably a precious metal composition primarily of gold or of pure gold. The filler material may also contain a binder such as wax. The wax binder may have a similar composition and concentration to the composition and concentration of the binder used to form the porous structure. A minimum binder concentration of at least about twenty percent (20%) by volume is preferred, and up to eighty-five percent (85%) by volume. Fifty percent (50%) or more of the overall weight of the filler composition is preferably of individual or alloyed particles, of any size, containing between 90% to 98.5% gold and between 1.5% to 8.5% silver, preferably 2% to 5%, with the remainder selected from the group of metals such as copper, zinc, aluminum, magnesium, gallium, indium, tin, or any of the platinum group metals and/or elements from the third or fourth groups of elements of the periodic table. The weight of the remainder should not exceed seven percent (7%) of the total weight. The other fifty percent (50%) of the filler composition may be composed entirely of gold, although other metals may be included, provided the silver content of the total filter composition is limited to no more than ten percent (10%) by weight, and the total of the other metals is also limited to ten percent (10%) by weight. The addition of metals, other than gold and silver, may be added to provide a melting gradient during melting of the filler material.

Figure 8:
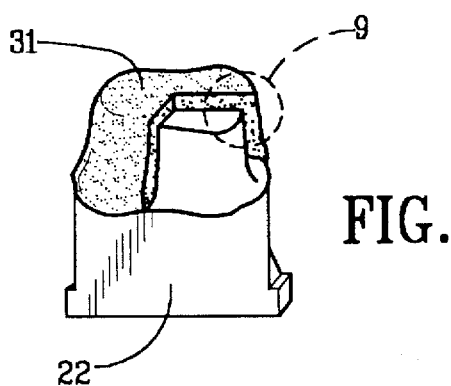
FIG. 8 is a perspective view of the finished coping upon completion of heat treatment and after removal of the investment with the finished coping shown sitting upon a die for convenience and having a section of the coping removed for illustrative purposes.
Figure 9:
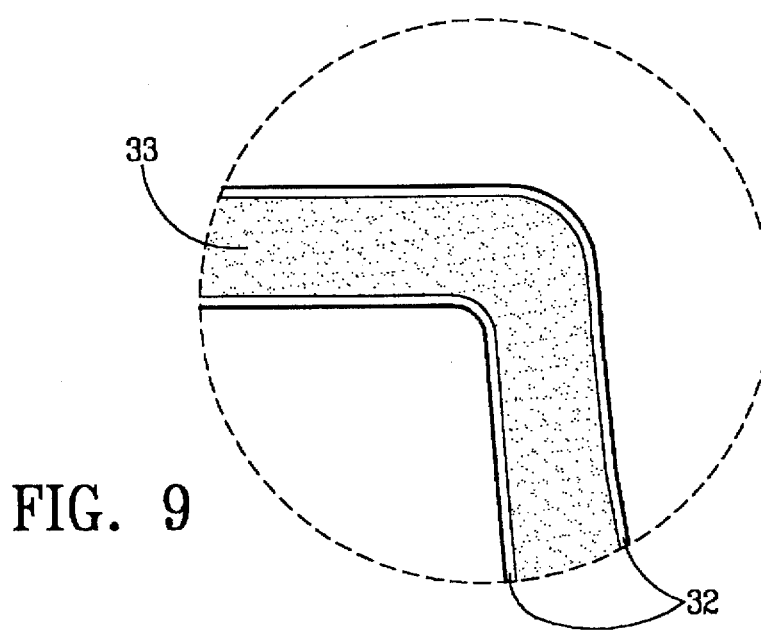
FIG. 9 is an exploded view of a section of the finished coping of FIG. 8 shown in cross section.

If wax is used as the binder in the filler, its composition is not critical, and any natural wax, mineral wax, organic wax, or synthetic wax composition may be used. The preferred wax for the filler is relatively soft and tacky, and should melt relatively cleanly, as should any other binder constituent, without leaving a significant residue. By using a relatively soft and tacky wax for the filler it may be readily compressed into a compacted strip 30 of any desired geometrical shape. The strip 30 may have any thickness generally between twenty-five (25) microns and ten (10) millimeters. The strip 30 is placed over the porous structure 29 which is still filled with the investment material 27 before being returned to the furnace for heat treatment. The strip 30 may be affixed to the porous structure 39 using any conventional tweezers or holder 40. Heat treatment occurs at a temperature sufficient to melt the filler into the voids of the porous structure 29 to densify the structure thereby forming upon removal of the investment 27 a finished dental coping 31. In FIG. 8 the finished dental coping 31 is shown seated for convenience upon the working die 22 and has a section removed therefrom to more clearly identify the final finished coping 31 as having a central body region 33 and substantially symmetrical inner and outer layers 32 as shown in FIG. 9. The central body region 33 is composed substantially of the base material metals and less than 50% of the filler metals whereas the inner and outer layers are substantially or entirely of gold.

What is claimed:

1. A method for forming, repairing or restoring a dental restoration comprising the steps of:

forming a base material comprising high-fusing temperature metal particles and a volatile binder composed substantially or entirely of wax;

applying the base material to a die;

shaping the base material upon said die into a desired configuration;

removing the shaped base material from the die;

combining particles of activated carbon with investment material to form a dental investment material having activated carbon in a concentration above at least 0.005 wt. % of the dental investment material;

filling the dental investment material into the shaped base material;

heat treating the shaped base material and the dental investment material at temperatures up to 1200° C. to vaporize the volatile binder from the base material for forming a porous structure with a void volume of at least 20%; and filling the porous structure with a filler material to form a finished dental restoration.

2. A method as defined in claim 1 wherein said base material further comprises low fusing temperature metal particles.

3. A method as defined in claim 2 wherein the porous structure is filled with said filler material and heat treated before removal of said dental investment material.

4. A method as defined in claim 3, wherein the concentration of said particles of activated carbon in said combined investment material is between 0.05 wt. % and 5.0 wt. %.

5. A method as defined in claim 4 wherein said filler material is composed substantially or entirely of gold.

6. A method as defined in claim 5 wherein said finished dental coping has a central region substantially composed of high fusing temperature metals and an outer layer substantially or entirely of gold.

7. A method as defined in claim 6 wherein at least fifty percent (50%) of the high-fusing particles in said base material has an average thickness of less than 1.5 microns.

8. A method as defined in claim 7 wherein said filler material includes a volatile wax binder and is in a compressed form.

9. A method as defined in claim 7 wherein said heat treatment of said base material is conducted in stages with a total heat treatment time of less than 30 minutes.

10. A method as defined in claim 1 wherein said base material is applied to said die at a temperature above room temperature.

11. A method as defined in claim 10 wherein said base material is applied to said die using an electric spatula.

* * * * *